United States Patent [19]

Goralski et al.

[11] 4,143,043

[45] Mar. 6, 1979

[54] 3,5-BIS(CHLOROMETHYLTHIO)-4-CYANOISOTHIAZOLE

[75] Inventors: Christian T. Goralski, Midland; George A. Burk, Bay City, both of Mich.

[73] Assignee: The Dow Chemical Company, Midland, Mich.

[21] Appl. No.: 881,089

[22] Filed: Feb. 24, 1978

Related U.S. Application Data

[62] Division of Ser. No. 726,346, Sep. 24, 1976, Pat. No. 4,094,880.

[51] Int. Cl.$^2$ ............................................. C07D 275/00
[52] U.S. Cl. ................................................. 260/302 S
[58] Field of Search ......................... 260/302 S, 302 A

[56] References Cited

U.S. PATENT DOCUMENTS 3,869,466  3/1975  Mixan ............................... 260/302 S

OTHER PUBLICATIONS

Hatchard, W. R., "Journal of Organic Chemistry," 29, pp. 660–668.

Primary Examiner—Donald G. Daus
Assistant Examiner—Lisa Jones

[57] ABSTRACT

Novel compounds, i.e. 3,5-bis(chloromethylthio)-4-cyanoisothiazole; 2,5-bis(chloromethylthio)-1,3,4-thiadiazole; and 3,5-bis(chloromethylthio)-1,2,4-thiadiazole are prepared by reacting an alkali metal aryl mercaptide with bromochloromethane in the presence of a quaternary ammonium salt. These novel compounds have microbiological activity and are also useful as intermediates in the preparation of the corresponding thiocyanomethylthio compounds which have antimicrobial activity.

1 Claim, No Drawings

3,5-BIS(CHLOROMETHYLTHIO)-4-CYANOISOTHIAZOLE

CROSS-REFERENCE TO RELATED APPLICATION

This is a division of application Ser. No. 726,346 filed Sept. 24, 1976, now U.S. Pat. No. 4,094,880.

BACKGROUND OF THE INVENTION

Few syntheses of mononuclear isothiazoles have been described.

W. R. Hatchard in *Journal of Organic Chemistry*, 29, pp. 660–668, teaches the synthesis of 3,5-dichloro-4-isothiazolecarbonitrile by the treatment of di(sodiomercapto)methylenemalononitrile with excess chlorine in boiling carbon tetrachloride. Hatchard also teaches reacting the salts of dimercaptomethylenemalononitrile with sulfur in boiling methanol to form salts of 3,5-dimercapto-4-isothiazolecarbonitrile, which in turn are converted to a variety of alkylthio-, acylthio-, and alkylsulfonylisothiazolecarbonitrile derivatives.

SUMMARY OF THE INVENTION

This invention concerns the new compounds (a) 3,5-bis(chloromethylthio)-4-cyanoisothiazole which corresponds to the formula

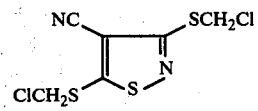

(b) 2,5-bis(chloromethylthio)-1,3,4-thiadiazole which corresponds to the formula

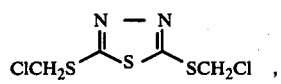

and (c) 3,5-bis(chloromethylthio)-1,2,4-thiadiazole which corresponds to the formula

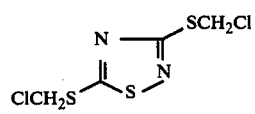

The novel compounds of the present invention are prepared by contacting in liquid phase the corresponding alkali metal aryl mercaptide with bromochloromethane in the presence of a small but catalytic amount of a quaternary ammonium salt having an aggregate carbon content of at least 10 carbon atoms (preferably from about 10 to about 35 carbon atoms). Reaction temperatures are normally selected in the range of from about 20° C. to 65° C.

The novel compounds of the present invention will react with potassium thiocyanate in dimethylformamide to form the corresponding thiocyanomethylthio compounds which are useful as antimicrobials. For example, 3,5-bis(chloromethylthio)-4-cyanoisothiazole will so react to form 4-cyano-3,5-bis(thiocyanomethylthio)isothiazole. Likewise, 2,5-bis(chloromethylthio)-1,3,4-thiadiazole will react to form 2,5-bis(thiocyanomethylthio)-1,3,4-thiadiazole and 3,5-bis(chloromethylthio)-1,2,4-thiadiazole will react to form 3,5-bis(thiocyanomethylthio)-1,2,4-thiadiazole. The two above-mentioned thiadiazoles are further described in U.S. Pat. No. 3,888,869 and the above-mentioned isothiazole is further described in U.S. Pat. No. 3,869,466.

DESCRIPTION OF SOME PREFERRED EMBODIMENTS

The first and second examples further illustrate the present invention and the manner by which the novel compounds of the present invention are produced. Example 3 illustrates how the novel compounds of the present invention are utilized in the preparation of the corresponding thiocyanomethylthio compounds. The product compounds in all the examples are identified by elemental analysis and/or nuclear magnetic resonance spectroscopy.

Example 1 — Production of 3,5-bis(chloromethylthio)-4-cyanoisothiazole

To a slurry of 10.90 g (0.05 mol) of the disodium salt of 4-cyano-3,5-dimercaptoisothiazole and 300 ml of bromochloromethane were added 0.44 g of benzyltriethylammonium bromide. The reaction mixture was slowly warmed from room temperature to 55° C. over a period of 5 hours. The reaction mixture was filtered to remove the sodium bromide by-product produced and the bromochloromethane was removed from the filtrate under reduced pressure leaving a tan solid. The solid was extracted with hot ether, and the ether solution was concentrated under reduced pressure to give 6.0 g of 3,5-bis(chloromethylthio)-4-cyanoisothiazole as a light yellow powder melting at 92° C. to 93° C. Further concentration gave an additional 2.1 g of the desired product. The combined total yield is 60 percent of theory.

Elemental analysis: Calculated for $C_6H_4Cl_2N_2S_3$: C, 26.57; H, 1.48; N, 10.33; S, 35.47. Found: C, 26.80; H, 1.73; N, 10.46; S, 36.18.

Example 2 — Production of 2,5-bis(chloromethylthio)-1,3,4-thiadiazole

This Example was conducted under essentially the same conditions as per Example 1. The amounts of reactants employed are as follows: 100 g (0.44 mol) of the dipotassium salt of 2,5-dimercapto-1,3,4-thiadiazole; 850 ml of bromochloromethane; and 2 g of benzyltriethylammonium bromide. The desired product was obtained as crystals melting at 64° C. to 65° C. The yield was 78% of theory.

Elemental analysis: Calculated for $C_4H_4Cl_2N_2S_3$: C, 19.40; H, 1.63; Cl, 28.70; N, 11.34; S, 39.90. Found: C, 19.90; H, 1.72; Cl, 28.50; N, 11.63; S, 39.20.

Example 3 — Preparation of 2,5-bis(thiocyanomethylthio)-1,3,4-thiadiazole

A solution of 38.0 g (0.154 mol) of 2,5-bis((chloromethyl)thio)-1,3,4-thiadiazole and 65 g (0.67 mol) of powdered anhydrous potassium thiocyanate in dimethylformamide was heated to 68° C. in 4 hours. The completed reaction mixture was stirred into 4 liters of ice water. After standing for 0.5 hours, the settled solid was filtered off and vacuum dried at 100° C. to give 45.0 g (95% yield) of the desired compound,

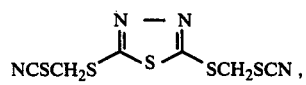

as a light tan solid melting at 113° C. to 115° C.

2,5-bis(chloromethylthio)-1,3,4-thiadiazole and 3,5-bis(chloromethylthio)-1,2,4-thiadiazole are particularly useful as antimicrobial agents for the control of bacteria and fungi. This is not to suggest that the above-mentioned compounds and mixtures thereof with usual additives are equally effective against all such organisms at the same concentration. For such use, the above-mentioned compounds can be employed in an unmodified form or dispersed on a finely divided solid and employed as a dust. Such mixtures can also be dispersed in water with the aid of a surface-active agent and the resulting emulsion employed as a spray. In other procedures, the above-mentioned compounds can be employed as the active constituents in solvent solutions, oil-in-water or water-in-oil emulsions. The augmented compositions are adapted to be formulated as concentrates and subsequently diluted with additional liquid or solid adjuvant to produce the ultimate treating compositions. Good results are obtained when employing compositions containing antimicrobial concentrations and usually from about 100 to about 500 parts by weight of one or more of the above-mentioned compounds per million parts of such compositions.

In representative activity tests, 2,5-bis(chloromethylthio)-1,3,4-thiadiazole is dispersed in warm melted nutrient agar which is then poured into petri dishes and allowed to solidify, the thiadiazole compound being employed in an amount sufficient to provide from 10 to 500 parts by weight thereof per million parts (ppm) of the ultimate agar composition. The surface of the agar is then inoculated with a variety of bacterial and fungal pest organisms, and the inoculated plates are incubated under conditions conducive to bacterial and fungal growth. Similar check plates in which the agar contains no active thiadiazole or other toxic compound are similarly inoculated and incubated.

In such operations, 2,5-bis(chloromethylthio)-1,3,4-thiadiazole gave 100% growth inhibition (kills) and control of the following organisms at the indicated concentrations in parts per million:

TABLE

| Antimicrobial Activity of 2,5-bis(chloromethylthio)-1,3,4-thiadiazole | |
|---|---|
| Organism | Concentration in ppm |
| T. mentagrophytes | 100 |
| A. niger | 500 |
| C. pelliculosa | 100 |
| P. pullulans | 500 |
| S. typhosa | 500 |
| M. phlei | 100 |
| R. nigricans | 100 |
| Trichoderm Sp. Madison P-42 | 100 |

3,5-bis(chloromethylthio)-4-cyanoisothiazole was similarly tested for antimicrobial activity and was found to give 100% growth inhibition and control of athlete's foot (*T. mentagrophytes*) at 500 ppm.

To illustrate the antimicrobial activity of the thiocyanomethylthio compounds which are prepared from the novel compounds of the present invention, 2,5-bis(thiocyanomethylthio)-1,3,4-thiadiazole, when tested for bactericidal and fungicidal activity using conventional agar dilution tests, gives complete growth inhibition against *Bacillus subtilis, Trichophyton mentagrophytes, Aspergillus terreus, Candida pelliculosa, Pullularia pullulans, Mycobacterium phlei, Rhizopus nigricans* and *Ceratocystis ips* at a concentration of one part per million; against *Staphylococcus aureus, Escherichia coli, Candida albicans, Salmonella typhosa* and *Trichoderma Sp. Madison P-42* at a concentration of 10 parts per million; and against *Aerobacter aerogenes* and *Pseudomonas Sp. Strain* 10 at a concentration of 100 parts per million. 3,5-bis(Thiocyanomethylthio)-1,2,4-thiadiazole displays similar activity. The activity of 4-cyano-3,5-bis(thiocyanomethylthio)isothiazole is described in U.S. Pat. No. 3,869,466.

What is claimed is:

1. The compound 3,5-bis(chloromethylthio)-4-cyanoisothiazole.